(12) United States Patent  (10) Patent No.: US 7,909,868 B2
Blom  (45) Date of Patent: Mar. 22, 2011

(54) VOICE PROSTHESIS AUTOMATIC FLANGE DEPLOYMENT CONFIRMATION METHOD AND DEVICE

(75) Inventor: Eric D. Blom, Carmel, IN (US)

(73) Assignee: Helix Medical, LLC, Plymouth, MI (US)

( * ) Notice: Subject to any disclaimer, the term of this patent is extended or adjusted under 35 U.S.C. 154(b) by 0 days.

(21) Appl. No.: 12/102,090

(22) Filed: Apr. 14, 2008

(65) Prior Publication Data

US 2009/0259310 A1 Oct. 15, 2009

(51) Int. Cl.
*A61F 2/20* (2006.01)
*A61F 2/08* (2006.01)
*A61F 11/00* (2006.01)

(52) U.S. Cl. .......... 623/9; 623/14.11; 623/902; 606/108

(58) Field of Classification Search ........... 623/9, 14.11, 623/23.64, 902; 128/207.14–207.16, 207.17, 128/207.29, 887; 600/29; 606/108
See application file for complete search history.

(56) References Cited

U.S. PATENT DOCUMENTS

| | | | |
|---|---|---|---|
| 4,435,853 A | 3/1984 | Blom et al. | |
| 4,614,516 A | 9/1986 | Blom et al. | |
| 4,911,716 A | 3/1990 | Blom et al. | |
| 5,300,119 A * | 4/1994 | Blom | 623/9 |
| 5,391,205 A * | 2/1995 | Knight | 623/9 |
| 5,507,809 A | 4/1996 | Blom | |
| 5,632,775 A * | 5/1997 | Suding et al. | 623/9 |
| 5,976,151 A * | 11/1999 | Siegbahn | 606/108 |
| 6,776,797 B1 | 8/2004 | Blom et al. | |
| RE39,923 E | 11/2007 | Blom | |
| 2005/0145252 A1 * | 7/2005 | Loyd et al. | 128/207.14 |

FOREIGN PATENT DOCUMENTS

DE 202008000670 U1 4/2008
WO 2005097001 A1 10/2005

OTHER PUBLICATIONS

Clinical Insights; InHealth Technologies; http://www.inhealth.com/educationalresourcesclininstghts.htm; (p. 1-11).

(Continued)

*Primary Examiner* — Brian E Pellegrino
*Assistant Examiner* — Marcia Hoffman
(74) *Attorney, Agent, or Firm* — Ronald W. Wangerow, Esq.; Harness, Dickey & Pierce, P.L.C.

(57) ABSTRACT

A gel cap is loaded on a folded flange of a voice prosthesis which is loaded on an end portion of an inserter, wherein a tip of the end portion is pressed against a valve flap of the voice prosthesis. The voice prosthesis includes a strap that is stretched for engagement with an attachment portion on the inserter. The voice prosthesis, gel cap, and inserter are inserted into the tracheoesophageal puncture. The patient then swallows fluids to cause the gel cap to dissolve to allow the esophageal flange to deploy, whereby upon deployment of the esophageal flange, the tip of the end portion of the inserter presses the valve flap open, allowing the inserter to move axially relative to the voice prosthesis until a stop collar of the inserter engages the voice prosthesis providing external visual confirmation to the user that the gel cap has dissolved and the esophageal flange has deployed.

4 Claims, 4 Drawing Sheets

OTHER PUBLICATIONS

Blom-Singer Voice Prostheses; InHealth Technologies; http://www.inhealth.com/featuredprdvppage1new.htm; (p. 1-4).

Voice Prostheses Accessories; InHealth Technologies; http://www.inhealth.com/featuredprdvpacc1new.htm; (p. 1-3).

Blom-Singer Voice Restoration Systems; InHealth Technologies; 37-365-01 Rev. D; (21 pages).

The Provox System; Atos Medical; Cat. 2006/2007; (36 pages).

* cited by examiner

VOICE PROSTHESIS AUTOMATIC FLANGE DEPLOYMENT CONFIRMATION METHOD AND DEVICE

FIELD

The present disclosure relates to a method and apparatus for the delivery, or placement, of, for example, a voice prosthesis device into a puncture provided in the tracheoesophageal wall of a speech restoration patient.

BACKGROUND

The statements in this section merely provide background information related to the present disclosure and may not constitute prior art.

A speech restoration technique for persons who have had their larynx (voice box) surgically removed is known wherein air from the trachea is diverted from its normal flow path out through the tracheostoma to a flow path through a voice prosthesis providing a more or less permanent passageway to the esophagus. Esophageal speech results. See U.S. Pat. Nos. 4,435,853; 4,614,516; and 4,911,716. Voice prostheses currently in use for providing controlled air pathways through tracheoesophageal punctures incorporate flexible retention collars. The retention collar lies against the esophageal surface of the tracheoesophageal wall to reduce the likelihood of dislodgement of the prosthesis from the puncture. While this configuration substantially improves retention, the presence of the large retention collar makes insertion of a prosthesis more difficult and traumatic to the tissue surrounding the tracheoesophageal puncture. A possibility inherent in difficult or traumatic prosthesis insertion is incomplete insertion. Incomplete insertion may result in aspiration of the prosthesis into the airway. The prosthesis may be expelled by coughing, requiring endoscopic retrieval from the airway. Additionally, concern about prosthesis insertion difficulty may prevent some patients and physicians from employing this method of voice restoration.

According to an aspect of the invention, a retainer soluble in fluid is provided for atraumatic insertion of a prosthesis into a puncture in the tracheoesophageal wall. The prosthesis includes a cylindrical body and a flexible first flange provided on an outside surface of the cylindrical body. The flange has a use orientation in which it projects generally outwardly from the outside surface of the body and an insertion orientation in which it is resiliently folded toward the axis of the body. The retainer retains the flange in its resiliently folded orientation.

To reduce the traumatic experience, the esophageal flange can be placed within a dissolvable capsule (referred to herein as "gel cap") to reduce the overall dimensions and facilitate the insertion through the tracheoesophageal puncture. Once in place, saliva or other liquid can be swallowed to dissolve the capsule and allow the esophageal flange to expand to its normal dimension and secure the voice prosthesis within the tracheoesophageal puncture.

In order to confirm proper deployment of the esophageal flange, a technician would typically insert a non-tipped end of a cotton swab or other elongated device into the prosthesis device and press against the valve flap at the distal end of the voice prosthesis. If the valve flap can be visually confirmed internally to open without obstruction, the technician could assume that the gel cap had dissolved and that the esophageal flange of the voice prosthesis had deployed to its proper location. This tactile and internal visual confirmation, unfortunately, is not always possible, for example, due to anatomical location of the voice prosthesis or in a voice prosthesis that has two valves. The clinician could also rotate the prosthesis device within the tracheoesophageal puncture to confirm proper deployment of the esophageal flange.

SUMMARY

With the method and apparatus of the present disclosure, the voice prosthesis is inserted into the tracheoesophageal puncture utilizing an inserter. The gel cap is positioned over the esophageal flange which is folded forward within the gel cap to provide ease of insertion into the tracheoesophageal puncture. The inserter includes an end portion which is longer than the voice prosthesis so that the tip of the end portion presses against a valve member of the voice prosthesis which is not allowed to open due to obstruction due to the esophageal flange being folded inward and retained by the gel cap. The prosthesis includes a strap portion which is hooked to a peg on the inserter. The strap portion is stretched so as to bias the voice prosthesis toward the peg. However, due to the valve member of the voice prosthesis being obstructed from opening by the folded flange in front of it, the strap portion of the voice prosthesis is maintained under load until the voice prosthesis is inserted into the tracheoesophageal puncture and the patient is allowed to swallow fluids to cause the gel cap to dissolve, thus permitting the esophageal flange to deploy to its proper position. The deployment of the tracheoesophageal flange removes the obstruction from the valve member such that the valve member is allowed to open and the stretch that is applied to the strap of the voice prosthesis causes the inserter to slide axially relative to the voice prosthesis until a stop collar of the inserter engages an end of the voice prosthesis. The movement of the inserter relative to the voice prosthesis is an external visual indicator to the clinician that the esophageal flange has properly deployed. The insertion technique of the present disclosure is gentler on the fistula, since rotation of the voice prosthesis is not needed for confirmation of flange deployment. Furthermore, the method is easier for the clinician since dissolving of the gel cap and deployment of the valve is verified by the tactile "pop-through" and external visual feedback by inspection of the location of the inserter relative to the voice prosthesis. The method also provides a gauged safe distance of pop through for a safer confirmation technique. A second step of inserting a second device to press against the valve flap is eliminated, thus avoiding a risk of injury to the posterior wall of the esophagus.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
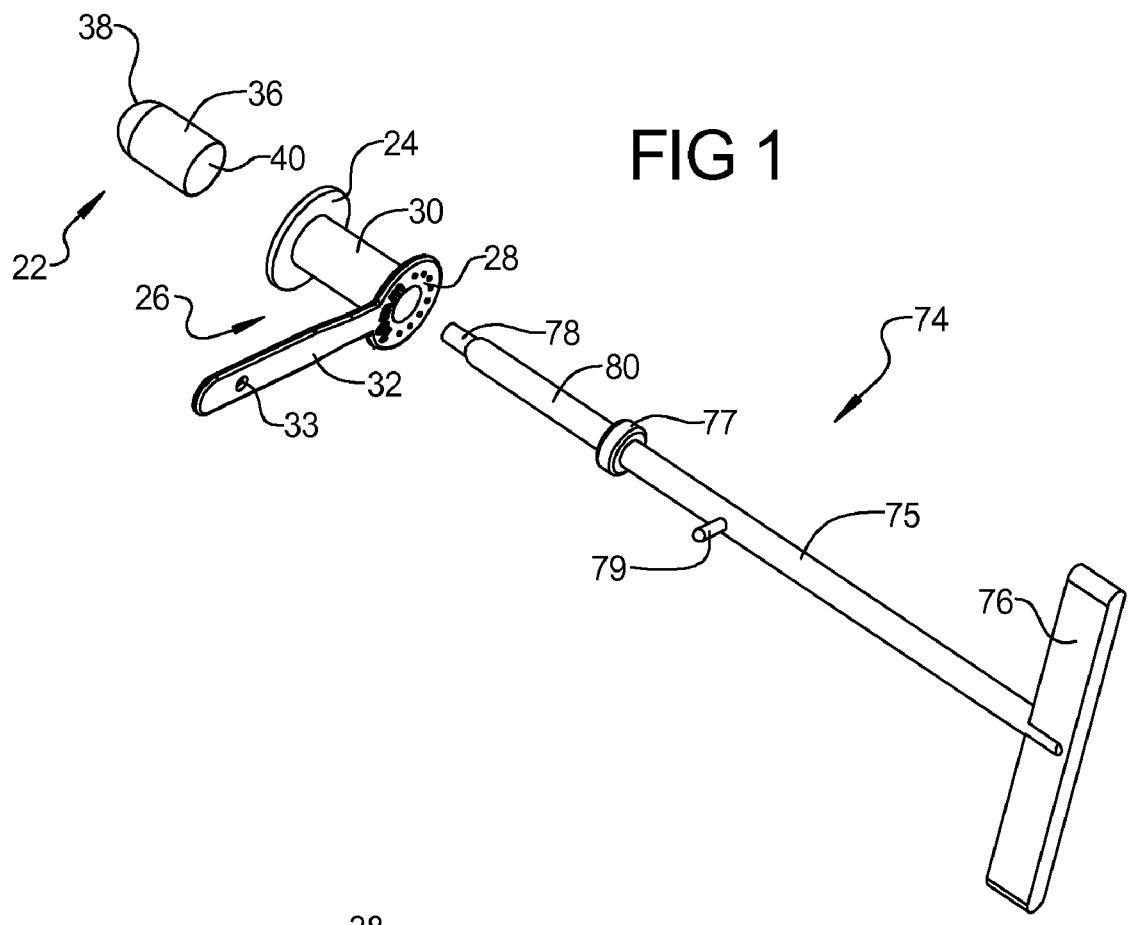
FIG. 1 is an exploded perspective view of the voice prosthesis, inserter, and gel cap according to the present disclosure in an unassembled state.

The following description is merely exemplary in nature and is not intended to limit the present disclosure, application, or uses. It should be understood that throughout the drawings, corresponding reference numerals indicate like or corresponding parts and features.

With reference to FIGS. 1-6 a method and apparatus for inserting a voice prosthesis according to the principles of the present disclosure will now be described. Initially, a gel cap 22 is placed over an esophageal flange 24 of a voice prosthesis 26. The voice prosthesis 26 includes an esophageal flange 24 and a tracheal flange 28 with a generally cylindrical hollow body 30 extending there between. Body 30 is open on both flanges 24, 28. A one-way valve 31 (best shown in FIG. 6) is disposed within body 30. A strap 32 extends outwardly from tracheal flange 28. Strap 32 has an opening 33 adjacent its end. The depiction of voice prosthesis 26 is representative of typical voice prosthesis. It should be appreciated, however, that voice prosthesis 26 can have a different configuration than that shown and still be inserted with the method and apparatus according to the present disclosure.

Figure 2:
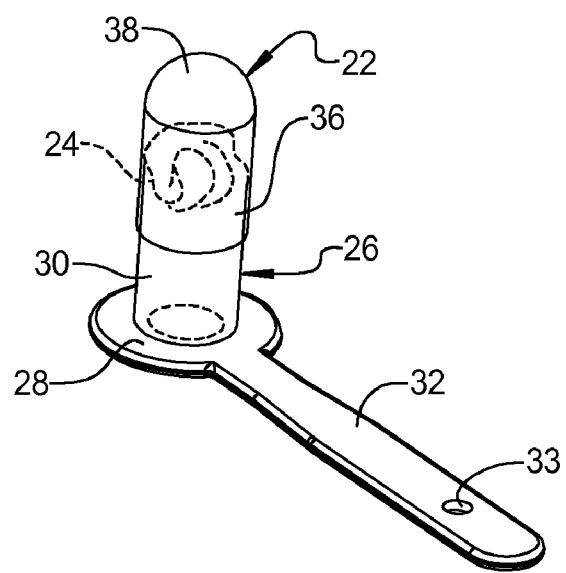
FIG. 2 is a perspective view of a voice prosthesis with a gel cap over the esophageal flange.
Figure 6:
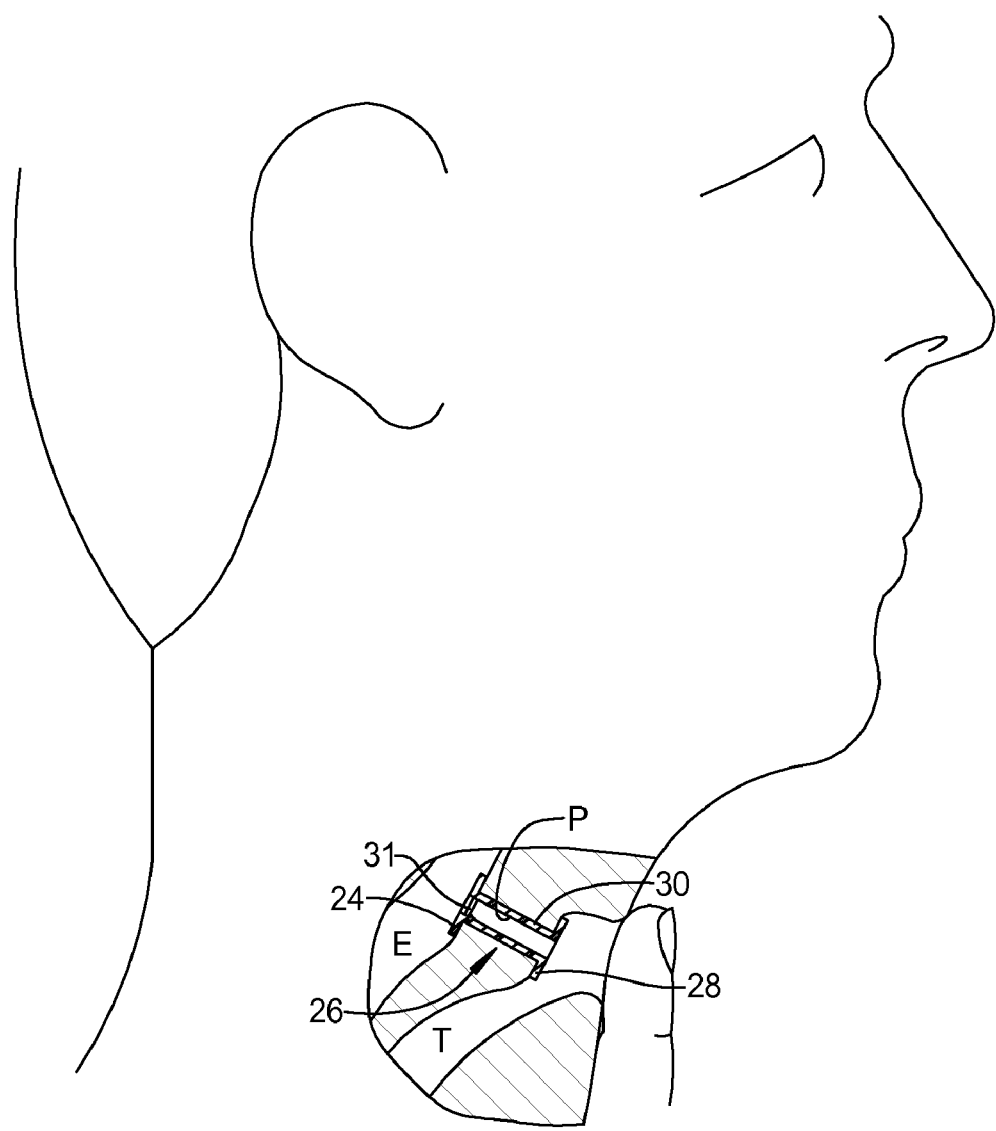
FIG. 6 is an assembled sectional view of a voice prosthesis in a puncture extending between the trachea and esophagus of a speech restoration patient.

A gel cap 22 includes a generally cylindrical body portion 36 and a hemispherical end portion 38. Body portion 36 and end portion 38 define an interior cavity 40 within which esophageal flange 24 and a portion of body 30 of voice prosthesis 26 can be inserted, as shown in FIG. 2. Gel cap 22 is dissolvable in liquid and facilitates the insertion of voice prosthesis 26 into a tracheoesophageal puncture (P) that extends between a trachea (T) and esophagus (E) of a user, as shown in FIG. 6. A dissolvable gel cap for retaining a flange of a voice prosthesis is disclosed in U.S. Pat. No. RE39,923, which is herein incorporated by reference in its entirety. In FIG. 6, gel cap 22 has been dissolved such that esophageal flange 24 is fully expanded within esophagus 48. Esophageal and tracheal flanges 24, 28 thereby retain voice prosthesis 26 in the tracheoesophageal puncture (P), as known in the art.

Figure 4:
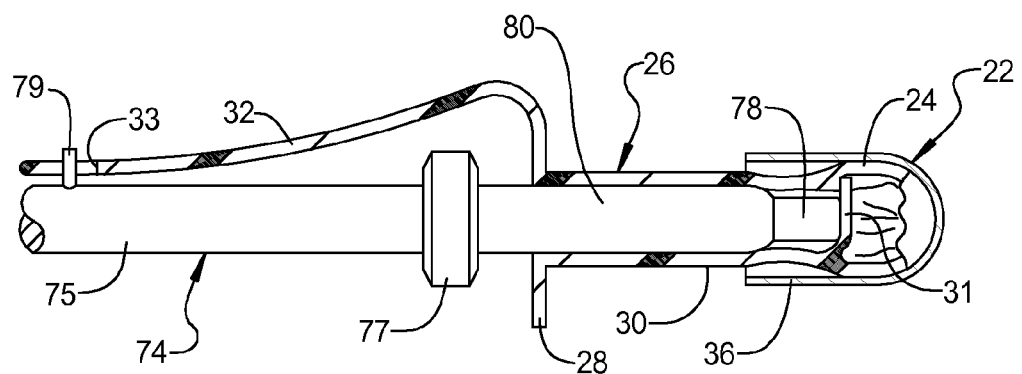
FIG. 4 is a sectional view of a voice prosthesis, gel cap, and inserter assembled as in FIG. 3.

An implement, such as an inserter 74, can be used to insert voice prosthesis 26 within tracheoesophageal puncture (P). Inserter 74 includes a stem 75 with a handle 76 at one end thereof. There is a radial stop collar 77 on stem 75 adjacent an end portion 80. Collar 77 limits the distance the end portion 80 of inserter 74 can be inserted into voice prosthesis 26. A tip 78 on the end portion 80 of stem 75 can be tapered to facilitate insertion of end portion 80 into the voice prosthesis 26 through the opening in the tracheal flange 28. A strap attachment portion, such as a peg 79, can be mounted on the inserter 74. The peg 79 can extend outwardly from stem 75 between collar 77 and handle 76. Peg 79 is configured to receive strap 32 with peg 79 extending through opening 33. Peg 79 is positioned so that strap 32 is stretched to engage with peg 79. The stretching of strap 32 helps keep voice prosthesis 26 on inserter 74 during handling. The end portion 80 of the inserter is longer than the voice prosthesis 26 such that when the gel cap 22 is installed on the esophageal flange 24, the folded esophageal flange 24 obstructs the valve member 31 from being opened. Thus, the tip 78 of the end portion 80 of the inserter 74 presses against the valve flap 31 with the stop collar 77 being spaced from the tracheal end of the voice prosthesis 26, as illustrated in FIG. 4. The stretch applied to the strap 32 applies a spring like force for biasing the voice prosthesis 26 toward the stop collar 77. It should be understood that alternative attachments portions can be used for engaging the strap 32 in a stretched position. Examples of attachment portions can include a clamp for engaging the strap, a slot for engaging an enlarged section of a strap, or other devices that can engage the strap 32 in a stretched condition.

Figure 3:
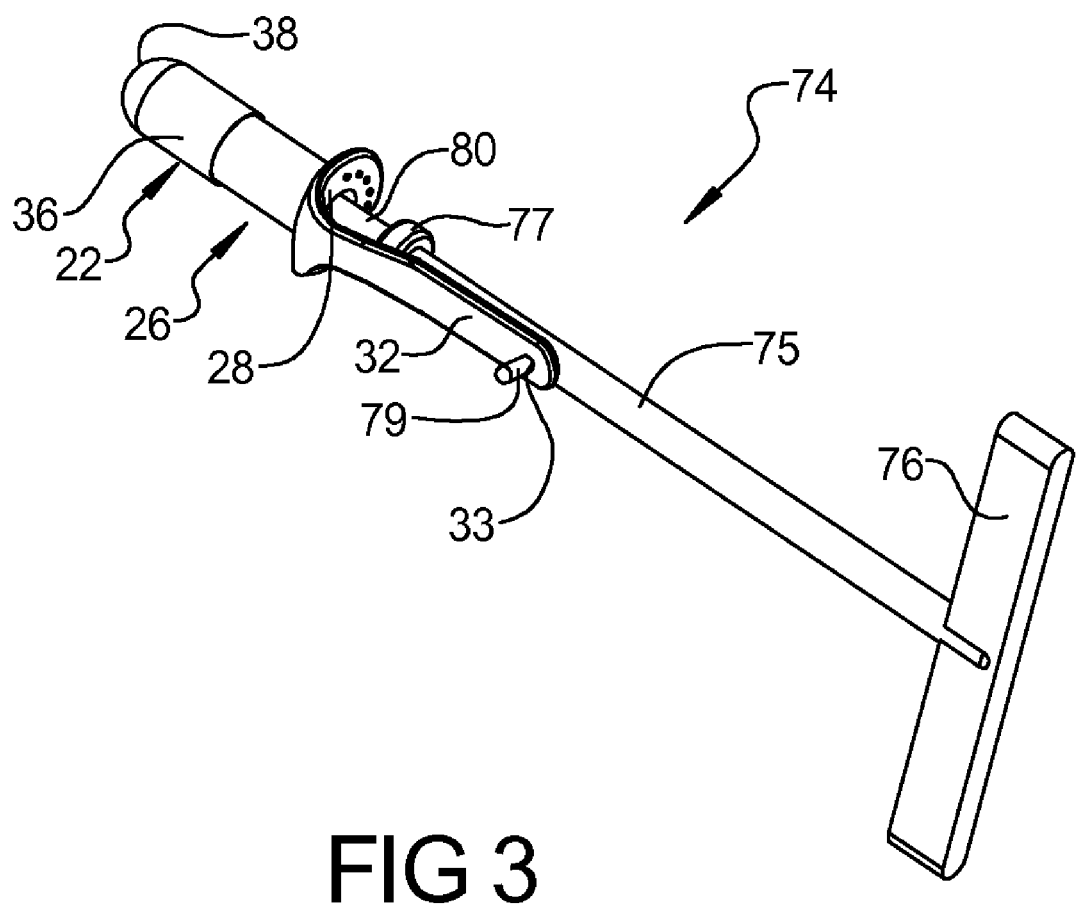
FIG. 3 is a perspective view of the components of FIG. 1 with the inserter engaged with the voice prosthesis and a gel cap assembled on the voice prosthesis.
Figure 5:
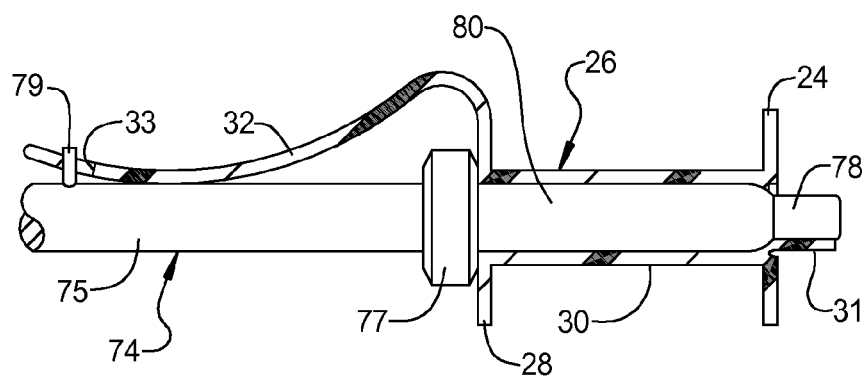
FIG. 5 is a sectional view of a voice prosthesis and inserter with the gel cap removed from the esophageal flange.

With the voice prosthesis 26 loaded on the inserter 74 and having the gel cap 22 installed on the esophageal flange 24 of the voice prosthesis 26, as illustrated in FIGS. 3 and 4, the voice prosthesis 26 is ready for insertion in the tracheoesophageal puncture P. Upon insertion of the voice prosthesis 26 into the tracheoesophageal puncture P, the patient is directed to swallow a fluid that is intended to dissolve the gel cap 22. As the gel cap 22 dissolves the esophageal flange 24 is deployed to its radial position as illustrated in FIG. 5. Simultaneously, the biasing force applied by the strap 32 causes the inserter 74 to move relative to the voice prosthesis 26 until the stop collar 77 engages the voice prosthesis 26 as the tip 78 of the inserter presses the valve flap 31 open, causing a visual indicator to the clinician that the gel cap 22 has dissolved and the esophageal flange 24 has deployed.

The clinician then removes the strap 32 from the peg 79 or other attachment portion of the inserter 74 and the inserter 74 is removed from the voice prosthesis 26. The clinician optionally may cut the strap 32 away from the voice prosthesis 26, and the installation is complete.

With the method and inserter device of the present disclosure, a clinician is provided with an externally visible indicator that the esophagea flange has properly deployed. The method can be used with a single valve or a multi-valve prosthesis, such as that disclosed in U.S. Pat. No. 5,507,809, wherein internal visual verification of opening of the distal valve flap is not possible.

What is claimed is:

1. A method of inserting a voice prosthesis into a tracheoesophageal puncture of a speech restoration patient, comprising:

loading a gel cap on a forward folded esophageal flange of the voice prosthesis;

loading the voice prosthesis on an end portion of an inserter, wherein the end portion has a length greater than a length of the voice prosthesis and a tip of the end portion is pressed against a valve flap of the voice prosthesis, said voice prosthesis including a strap that is stretched into engagement with an attachment portion of the inserter, said inserter including a stop collar, said forward folded esophageal flange engaging said valve flap in a closed position and obstructing said valve flap from opening from the closed position when the gel cap is in a non-dissolved state such that said stop collar is spaced from said voice prosthesis when said strap is stretched into engagement with the attachment portion, wherein said valve flap being obstructed from opening maintains said voice prosthesis spaced apart from said stop collar when said strap is stretched into engagement with the attachment portion of said inserter thereby applying a biasing force to said voice prosthesis toward said stop collar;

inserting the voice prosthesis, gel cap and inserter into the tracheoesophageal puncture; and having the speech restoration patient swallow fluids to thereby cause said gel cap to dissolve to allow the esophageal flange to deploy, whereby upon deployment of said esophageal flange, the biasing force applied to said voice prosthesis toward said stop collar by the stretched strap causes the inserter to move relative to the voice prosthesis and into engagement with the stop collar upon dissolving of the gel cap and deployment of said esophageal flange, which allows the inserter tip of the end portion of the inserter to press open the valve flap from the closed position and allows the inserter to move relative to the voice prosthesis until the stop collar engages the voice prosthesis providing visible, external confirmation that the gel cap has dissolved and the internally located, not visible esophageal flange has deployed.

2. The method according to claim 1, wherein said attachment portion includes a peg extending from said inserter.

3. A combination voice prosthesis and inserter device for inserting the voice prosthesis into a tracheoesophageal puncture of a speech restoration patient, comprising:

the voice prosthesis including an elongated body portion having an esophageal flange at a first end and a tracheal flange at a second end, said voice prosthesis further including a valve flap disposed in said elongated body adjacent to said esophageal flange, said voice prosthesis including a strap extending from said tracheal flange, said voice prosthesis defining a first distance extending from said tracheal flange to said valve flap;

a dissolvable retainer device disposed over said esophageal flange and retaining said esophageal flange in an axially folded position, wherein said esophageal flange in said axially folded position engages said valve flap in a closed position and obstructs opening of said valve flap from the closed position; and an inserter having an end portion extending from a stop collar portion, said end portion having a length greater than said first distance, said inserter including a stem portion disposed on an opposite side of said stop collar from said end portion and including an attachment portion thereon, wherein said end portion of said inserter is inserted in said body portion of said voice prosthesis so that a tip of said end portion is disposed against said valve flap and said strap is stretched such that said strap is engaged with said attachment portion so as to apply a bias force to said voice prosthesis toward said stop collar;

wherein said tracheal flange is spaced from said stop collar when said strap is applying said bias force and said end portion tip is disposed against said valve flap, which is obstructed from opening from the closed position by the esophageal flange; wherein upon dissolving of said dissolvable retainer to allow said esophageal flange to deploy, said bias force causes said end tip to press open said valve flap, which allows said inserter to move relative to said voice prosthesis until said stop collar engages said voice prosthesis providing visible, external confirmation that the internally located, not visible esophageal flange has deployed being retained in the axially folded position by said dissolvable retainer being in a non-dissolved state.

4. The combination according to claim 3, wherein said attachment portion includes a peg extending from said inserter.

* * * * *

UNITED STATES PATENT AND TRADEMARK OFFICE
CERTIFICATE OF CORRECTION

| | | |
|---|---|---|
| PATENT NO. | : 7,909,868 B2 | Page 1 of 1 |
| APPLICATION NO. | : 12/102090 | |
| DATED | : March 22, 2011 | |
| INVENTOR(S) | : Eric D. Blom | |

It is certified that error appears in the above-identified patent and that said Letters Patent is hereby corrected as shown below:

At column 6, claim number 3, line number 17, after "esophageal flange," insert --being retained in the axially folded position by said dissolvable retainer being in a non-dissolved state;--.

At column 6, claim number 3, line number 24, after "flange has deployed," delete "being retained in the axially folded position by said dissolvable retainer being in a non-dissolved state".

Signed and Sealed this
Twenty-eighth Day of June, 2011

David J. Kappos
*Director of the United States Patent and Trademark Office*